US008367047B2

(12) United States Patent
Van Nguyen et al.

(10) Patent No.: US 8,367,047 B2
(45) Date of Patent: Feb. 5, 2013

(54) HAIR COMPOSITIONS

(75) Inventors: Nghi Van Nguyen, Edison, NJ (US);
Cynthia Espino, Princeton, NJ (US);
David Cannell, Plainfield, NJ (US)

(73) Assignee: L'Oreal, Paris (FR)

( * ) Notice: Subject to any disclaimer, the term of this patent is extended or adjusted under 35 U.S.C. 154(b) by 1288 days.

(21) Appl. No.: 10/323,654

(22) Filed: Dec. 20, 2002

(65) Prior Publication Data

US 2004/0120919 A1  Jun. 24, 2004

(51) Int. Cl.
*A61Q 5/00* (2006.01)

(52) U.S. Cl. ............ 424/70.16; 424/70.122; 424/70.31

(58) Field of Classification Search .................. None
See application file for complete search history.

(56) References Cited

U.S. PATENT DOCUMENTS

| 5,988,180 | A * | 11/1999 | Bergstrom .................. 132/204 |
| 6,221,389 | B1 | 4/2001 | Cannell et al. |
| 6,524,614 | B2 * | 2/2003 | Cannell et al. ............. 424/450 |
| 6,706,674 | B2 * | 3/2004 | Cincotta et al. ............ 510/119 |
| 2001/0009672 | A1 | 7/2001 | Cannell et al. |
| 2002/0197227 | A1 * | 12/2002 | Scholz ...................... 424/70.12 |

FOREIGN PATENT DOCUMENTS

| DE | 100 60 814 | 6/2002 |
| EP | 0 511 652 | 11/1992 |
| JP | 2002-504113 | 2/2002 |
| JP | 2002-531478 | 9/2002 |
| JP | 2002-531485 | 9/2002 |
| WO | WO 98/56333 | 12/1998 |
| WO | WO 00/33798 | 6/2000 |
| WO | WO 00/33808 | 6/2000 |

OTHER PUBLICATIONS

Chinese Office Action w/English Translation.
Japanese Office Action w/English Translation.
Korean Office Action w/English Translation.
Memo concerning the Action as received in the corresponding Mexican Patent Application No. PA/a/2003/011505 dated Sep. 2, 2009.
Communication as received in the corresponding European Patent Application No. 03 293238.6 dated Jun. 21, 2011.
Communication as received in the corresponding European Patent Application No. 03 293 238.6-1521 dated Feb. 21, 2012.
Chinese Office Action w/English Translation, Mar. 2006.
Japanese Office Action w/English Translation, Mar. 2006.
Korean Office Action w/English Translation, Apr. 2006.

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

The present invention relates to hair compositions comprising at least one lecithin, at least one amphoteric surfactant, at least one nonionic surfactant, at least one film forming polymer, and at least one cationic polymer. The compositions are preferably used to maintain hair's natural shape and/or its curl definition.

12 Claims, 1 Drawing Sheet

Shampoo + LAN + 0.5% Polymer JR 30M + 0.5% Amphomer LV-71
Shampoo + LAN + 0.5% Amphomer LV-71
Shampoo + LAN + 0.5% Polymer JR 30M
Shampoo + LAN
Water

HAIR COMPOSITIONS

FIELD OF THE INVENTION

The present invention relates to hair compositions comprising at least one lecithin, at least one amphoteric surfactant, at least one nonionic surfactant, at least one film forming polymer, and at least one cationic polymer. Also preferably present in the invention compositions is water. The compositions are preferably used to maintain hair's natural shape and/or its curl definition.

BACKGROUND OF THE INVENTION

Frizzy hair is one of the biggest problems encountered when hair is subjected to higher humidity (e.g., relative humidities of 80% and more). Frizzy hair is or becomes unmanageable and undisciplined. Such problems are often exacerbated in people with curly hair, either naturally curly or "permed" curly, leading to what is colloquially termed a "bad hair day". In such a case, hair loses its natural shape and/or its curl definition. Thus, hair compositions that address these problems are quite desirable.

SUMMARY OF THE INVENTION

The present inventors have now discovered compositions that address the above problems. These compositions comprise at least one lecithin, at least one amphoteric surfactant, at least one nonionic surfactant, at least one film forming polymer, and at least one cationic polymer. The first three components listed (i.e., at least one lecithin, at least one amphoteric surfactant, at least one nonionic surfactant) are sometimes referred to as a "LAN system" or simply as "LAN" herein. Preferably, the film forming polymer is a non-neutralized resin.

BRIEF DESCRIPTION OF THE DRAWINGS

FIG. 1 shows the effects of various compositions on hair swatch frizziness under high humidity exposure.

DETAILED DESCRIPTION OF THE PRESENT INVENTION

Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention include the types described above and may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

In the present invention, lecithin is preferably used in an amount greater than 0 to about 5% by weight of the composition as a whole. Since lecithin itself is not necessarily a pure raw material and may have free glycerides, glycerin, fatty acids, and soaps, adjustments in this amount may need to be made, i.e., one source of lecithin may require different ratios of nonionic and amphoteric surfactants than another to achieve, e.g., maximum clarity of solution. Preferably, the composition of the invention forms a clear solution, though the purpose of the invention is achieved just as effectively with a cloudy or slightly cloudy solution, etc.

A group of phospholipids which can be used in the present invention as lecithins are multifunctional biomimetic phospholipids, including, for example, the following multifunctional biomimetic phospholipids manufactured by Mona Industries: PHOSPHOLIPID PTC, PHOSPHOLIPID CDM, PHOSPHOLIPID SV, PHOSPHOLIPID GLA, and PHOSPHOLIPID EFA.

The amphoteric surfactants useful in the present invention include, but are not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Cocamphodipropionate is particularly preferred, for example, MIRANOL C2M-SF Conc. (disodium cocamphodipropionate), in its salt-free form, available from Rhône-Poulenc. Also preferred is CROSULTAINE C-50 (cocamidopropyl hydroxysultaine), available from Croda. The amphoteric surfactants are preferably present in the composition in an amount ranging from about 2 to 10% by weight of the composition as a whole when 5% of the lecithin is used. When the lecithin/amphoteric/nonionic system is employed as a carrier for a water-insoluble polymer or resin, the amphoteric surfactants are preferably present in the composition in an amount ranging from about 6 to 10% by weight. When the lecithin/amphoteric/nonionic system is employed as a carrier for a lipophilic material, the amphoteric surfactants are preferably present in the composition in an amount ranging from about 4 to 8% by weight. Other amphoteric surfactants useful in the present invention include disodium wheatgermimido PEG-2 sulfosuccinate, available under the trade name MACKANATE WGD from McIntyre Group Ltd. and disodium soyamphodiacetate, available under the trade name MACKAM 2S from McIntyre Group Ltd. Usually the amphoteric is used as a 40% active material product, with the above percentages reflecting active material.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10-25, more preferably from 10-20 moles.

Nonionic surfactants may be selected from, but are not limited to, the following:

| # of Cs | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | Arlasolve 200, available from ICI Surfactants |
| C-18 | Steareth-10 | Volpo S-10, available from Croda Chemicals Ltd. |
| C-18 | Steareth-16 | Solulan-16, available from Amerchol Corp. |
| C-18 | Steareth-20 | BRIJ 78, available from ICI Surfactants |
| C-18 | Steareth-25 | Solulan-25, available from Amerchol Corp. |
| C-18= | Oleth-10 | BRIJ 97, available from ICI Surfactants |
| C-18= | Oleth-20 | Volpo-20, available from Croda Chemicals Ltd. |

Alkyl polyglucose surfactants sold under the name PLANTAREN, available from Henkel, may also be used. The nonionic surfactant is preferably present in an amount of about 5 to 20% by weight relative to the weight of the whole composition when 5% lecithin is used. More preferably, the nonionic surfactant is present in an amount of about 10 to 20% by weight.

In one preferred embodiment of the composition of the present invention, within the LAN in particular, the lecithin, the amphoteric surfactant, and the nonionic surfactant are present in the composition such that the nonionic surfactant and the amphoteric surfactant are each present in an amount by weight greater than the amount of lecithin. In a more preferred embodiment, the amount of lecithin in the composition is kept fixed while the amounts of the amphoteric and nonionic surfactants are increased. In a still more preferred embodiment, calculating the lecithin as present at a value of 1, the phospholipid, amphoteric surfactant and nonionic surfactant are preferably present in the composition in a ratio ranging from about 1/0.8/2 and above by weight relative to the whole composition, i.e., where the amounts of the surfactants can be increased independently of each other but the amount of lecithin stays fixed. The ratio is considered to be "above" 1/0.8/2 when the amount of either of the surfactants increases. Another preferable range is from about 1/1.2/2 and above. A further preferred ratio is about 1/1.2/3 and above, and more preferably above about 1/1.2/4. The loading capability for hydrophobes carried by the LAN system of the present invention is maximized if the ratio of nonionic surfactant to lecithin is minimized, with bilayers formed by the lecithin still being solubilized, because an excess of nonionic surfactant may disrupt the organized structure.

In one preferred embodiment, the composition of the present invention comprises ALCOLEC S (soy lecithin), MIRANOL C2M-SF Conc. (disodium cocamphodipropionate, an amphoteric surfactant), ARLASOLVE 200 (IsoCeteth-20, a nonionic surfactant) in a ratio of 5/6/10 (1:1.2:2) and 5/6/20 (1:1.2:4) wherein the ratios are calculated by weight relative to the whole composition. Typically, LAN compositions of the invention can resist storage at 45° C. for three months or more, which would predict that they have a shelf life at room temperature of at least three years.

Film forming polymers useful herein are non-neutralized or partially neutralized, preferably non-neutralized, polymers and resins, most preferably non-neutralized resins, wherein the polymers and resins include but are not limited to those containing carboxyl moieties, such as acrylates and other carboxy polymers. Typically, water-insoluble polymers and resins have to be neutralized to about 90% of their carboxyl moieties to make them water soluble for the purpose of formulating products in aqueous solution and for the purpose of making products which have good non-build-up properties, i.e., can be easily washed off the hair after use. However, when used with the compositions of the present invention complete, some (e.g., up to 90%) or no neutralization is needed to effectively use these polymers/resins. It is believed that the combination of the lecithin, the nonionic surfactant, and the amphoteric surfactant of the present invention provides the usefulness of the water-insoluble polymers or resins.

The following are examples of film forming polymers that can be incorporated into the compositions of the present invention. The list is not intended to be limiting:

AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/methacrylic acid), and ULTRAHOLD STRONG from BASF (acrylic acid/ethyl acrylate/t-butyl acrylamide).

Unneutralized or partially neutralized water-insoluble latexes can also be used as invention film-forming polymers. Included are the following latexes:

AMERHOLD DR-25 from Amerchol (acrylic acid/methacrylic acid/acrylates/methacrylates), LUVIMER 36D from BASF (ethyl acrylate/t-butyl acrylate/methacrylic acid), and ACUDYNE 258 from Rohm & Haas (acrylic acid/methacrylic acid/acrylates/methacrylates/hydroxy ester acrylates).

The film forming polymer is preferably present in amounts ranging from 0.1% to 15 wt. % based on total weight of composition. The concentrations of LAN and film former can be adjusted by one of ordinary skill in view of this disclosure, as can neutralization extent.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Meyhall; and MERQUAT 100 and 280, a dimethyl dialkyl ammonium chloride (polyquaternium 6) available from CALGON. The cationic polymer is preferably present in an amount of about 0.1% to about 15% relative to the total weight of the inventive composition. Amounts of cationic polymer and other invention components can be adjusted relative to one another by one of ordinary skill in view of this disclosure.

The invention compositions preferably also further comprise water, and can in addition contain ingredients such as silicones, anionic surfactants, organic salts, inorganic salts, proteins, hair dyes, water-soluble polymers, quaternary ammonium compounds, complex and simple carbohydrates, amino acids, preservatives and fragrances.

The composition of the invention preferably has a pH ranging from 2-12.

Another embodiment of the present invention is drawn to a process for preparing the invention compositions. This process preferably comprises: (a) combining the following ingredients to obtain a mixture: at least one lecithin, at least one nonionic surfactant, and at least one amphoteric surfactant, where the nonionic surfactant and amphoteric surfactant are each present in an amount by weight equal to or greater than the amount of the lecithin, (b) heating the mixture obtained in step (a), and (c) adding an aqueous solution to the heated mixture to obtain the desired carrier system. Water-insoluble ingredients may be added in step (a). The mixture is preferably heated at a temperature of 65° C. to 85° C., depending on the melting points of the solid surfactants.

More specifically, the preparation of the LAN system of the present invention may preferably be carried out as follows. Lecithin (L) is dispersed in water. The water-insoluble material is combined with nonionic surfactant(s) (N) at appropriate ratios and added to the lecithin/water dispersion. An amphoteric surfactant (A) is added and the mixture is heated, preferably to a temperature of from 75° C. to 85° C. The combination of these ingredients results in a solution which is clear to slightly hazy and is referred to as the "LAN," which can then be used as a "raw material" to make finished products.

Alternatively, lecithin, amphoteric surfactant(s) and nonionic surfactant(s) can be weighed to appropriate ratios and heated to 70° C. with stirring. Water is then added q.s. at the same temperature. Another alternative method of preparation comprises adding the water-insoluble ingredient with mixing after solutions have cooled. This last alternative method helps protect heat-sensitive water-insoluble ingredients.

The resulting compositions may vary from clear to slightly hazy and are infinitely dilutable with water. The slight haze can be overcome by adjusting the ratio of lecithin to the surfactants, adjusting pH, or reducing concentrations of water-insoluble ingredients.

Once the LAN is prepared the film forming polymer and cationic polymer can be added thereto and stirred at from, e.g., 50° C. to 85° C., until homogeneous if desired.

With respect to hair compositions, the present invention compositions can take any form, including hair products, e.g., for normal hair, color-treated hair, dry hair, fine hair, and damaged hair. For each type of hair, the composition can be used to create a regimen comprising shampoo, conditioner, styling and deep treatment, (i.e., deep conditioner). Compositions for these products preferably contain lecithin (L), at least one amphoteric surfactant (A), such as disodium cocoamphodipropionate, and at least one nonionic surfactant (N), e.g., a blend of Oleth-10 and PPG-5-Ceteth-20 as LAN. Additional nonionic, amphoteric, and also anionic surfactants can be added. The compositions may further contain at least one water-insoluble ingredient (also referred to as a hydrophobe) such as olive, mineral, or other oils, octyl salicylate, Vitamin E (Tocopherol), octyl methoxycinnamate, and ceramides including 2-oleamido-1,3-octadecanediol.

In general, the concentration of the LAN may be increased within each regimen from shampoo to conditioner to deep treatment. Thus, the deep treatment formulations preferably have the most concentrated hydrophobe-carrying LAN.

The compositions of the invention can further comprise proteins including hydrolyzed soy protein, lauryldimonium hydrolyzed soy protein (cationic Soya protein) and wheat amino acids. The proteins can also include corn, wheat, milk, or silk proteins, collagens, keratins, or others. Furthermore, taurine and arginine hydrochloride may be associated therein to maximize protein binding to the hair Further, shampoos, conditioners, styling compositions and deep treatments within the scope of the present invention may be used on hair which has been treated, e.g., with color (dye or bleach) or chemicals (permanent wave or straightening), or which is dry or fine and show significant substantivity for the hair. Invention compositions preferably take the following forms: shampoo, gel, cream, foam, pomades, aerosol, spray, etc.

Further descriptions of components useful herein, including the LAN, cationic polymers, and film forming polymers, can be found in U.S. Pat. Nos. 6,015,574, 6,440,456, 6,436, 436 and 6,221,389, and in U.S. application Ser. Nos. 09/205, 692 and 09/207,656, all of which are incorporated herein by reference.

EXAMPLES

The following Examples illustrate various aspects and preferred embodiments of the invention, but are not limiting in any way. The test used to assess the performance of the invention compositions is based on the fact that curly hair, under high humidity for 8 hours, becomes slack (loses its curliness) and frizzed (increased in volume).

Hair swatches were shampooed, rinsed, curled and let to dry overnight and then put into a humidity chamber for 8 hours at 90% relative humidity. In high humidity, hair will normally frizz and lose its curl definition. Treated hair, however, is less frizzy and its curl definition is retained. It is possible to determine the extent of frizziness of each hair swatch by determining the percent change in area of the image of hair swatches before and after being subjected to high humidity. In the tests below the following equipment was used for this determination:

SigmaScan Image Analysis Version 3.00 for Windows by Jandal Scientific Software Co.
Visioneer OneTouch 8600 Scanner
Visioneer PaperPort Scanner Program Version 6.1 Deluxe
Procedure
I. Anti Frizz Shampoo Preparation
1. Take weight measurements of beaker and spin bar.
2. Combine 0.1 g Lecithin in a 150 ml beaker
5.6 g Mackam (amphoteric surfactant)
9.3 g Procetyl (nonionic surfactant)
3. Heat to 70° C. while stirring.
4. Stir until homogeneous.
5. Add 45.6 g hot water (approx. 70° C.).
6. Stir at 70° C. until homogeneous.
7. Add 0.5 g Film Former
0.5 g Quats (JR-30M) (cationic polymer)
8. Stir at 70° C. until homogeneous.
9. Cool to 50° C. in a water bath.
10. Add 30.0 g SLES
11. Stir until homogeneous.
12. Cool at room temperature.
13. Adjust to pH ~6 using e.g., 50% $H_3PO_4$.
14. Adjust to 100 mL of shampoo by adding $H_2O$.
II. Hair Treatment
1. Shampoo hair swatch with 1 g of shampoo for 1 minute, rinsed for 30 seconds with running warm water then tightly wound onto a pegboard with both ends secured with a rubber band.
2. Leave to dry in the oven at 50° C. from 1 hour.
3. Take hair swatches out of the oven to equilibrate at ambient conditions overnight.
4. Carefully remove pegs from the pegboard and cut the end of the hair swatch where it curves down the board to keep the hair swatch straight.
5. Obtain the image of the hair by photocopying the hair swatch against a white background.
6. Put the hair swatch into the humidity chamber at 90% RH for 8 hours, and again the image is taken by photocopying.

7. Calculate percent change using the areas of the images. Percent change is 100%×(total area of step 6 divided by total area of step 5).

In the Examples below the reported concentration is percent by weight.

As used below, the following abbreviations and names have the following meanings:

SLES: sodium lauryl ether sulfate
Polymer JR 30M: polyquaternium 10
Amphomer LV-71: octylacrylamide/acrylates/butylaminoethyl methacrylate copolymers)
Jaguar C135-S: guar hydroxypropyltrimonium chloride Performance of the LAN, Non-Neutralized Resin, and Cationic Polymer Following the above procedure, hair was treated with water, SLES+LAN, SLES+LAN+0.5% cationic polymer (Polymer JR 30M), SLES+LAN+0.5% non-neutralized resin (Amphomer LV-71), and SLES+LAN+0.5% Polymer JR 30M+0.5% Amphomer LV-71. The measured area of the hair swatches was 95202, 94276, 96353, 110202, and 51454 pixels, respectively. The data showed that the system containing LAN, cationic polymer, and non-neutralized resin is highly effective in retaining curl definition. The results are also shown graphically in FIG. 1.

Effects on the Concentration of the Cationic Polymer

Hair was treated with the following systems: SLES, and SLES+LAN+0.5% Amphomer LV-71+0.10%, 0.25%, 0.50%, 0.75% Jaguar C13S. The results are shown in Table 1.

TABLE 1

Percent Change in the Area of Hair Treated with the LAN + Non-neutralized Resin + Various Concentrations of Cationic Polymer

| % of Jaguar C13S | % Change |
| --- | --- |
| 0 | 448 |
| 0.10 | 355 |
| 0.25 | 232 |
| 0.50 | 205 |
| 0.75 | 161 |

The data shows that as the concentration of the cationic polymer increased, the performance of the LAN+non-neutralized resin+cationic polymer in retaining curl definition increases.

Effects on the Concentration of the Non-Neutralized Resin

Hair was treated with the following systems: SLES, and SLES+LAN+0.5% Polymer JR 30M+0.20%, 0.50%, 0.80%, 1.00% Amphomer LV-71. The results are shown in Table 2.

TABLE 2

Percent Change in the Area of Hair Treated with the LAN + Cationic Polymer + Various Concentrations of Non-neutralized Resin

| % of Amphomer LV-71 | % Change |
| --- | --- |
| 0 | 448 |
| 0.20 | 392 |
| 0.50 | 179 |
| 0.80 | 145 |
| 1.00 | 112 |

The data shows that as the concentration of the non-neutralized resin increases, the performance of the LAN+non-neutralized resin+cationic polymer in retaining curl definition increased.

Effects of Various Non-Neutralized Resins

Hair was treated with the following systems: SLES, and SLES+LAN+0.5% Polymer JR 30M+0.20%, 0.50%, 0.80%, 1.00% of various non-neutralized resins. The results are shown in Table 3.

TABLE 3

Percent Change in the Area of Hair Treated with the LAN + Cationic Polymer + Various Concentrations of Various Non-neutralized Resins

| Resin | % of Resin | % Change |
| --- | --- | --- |
| SLES | 0 | 448 |
| Resyn 28–2930 | 0.20 | 442 |
| | 0.50 | 287 |
| | 0.80 | 201 |
| | 1.00 | 276 |
| Luvimer 100P | 0.20 | 550 |
| | 0.50 | 383 |
| | 0.80 | 459 |
| | 1.00 | 92 |
| Luvimer 36D | 0.20 | 165 |
| | 0.50 | 244 |
| | 0.80 | 181 |
| | 1.00 | 189 |
| Balance CR | 0.20 | 459 |
| | 0.50 | 410 |
| | 0.80 | 424 |
| | 1.00 | 321 |
| Acudyne 258 | 0.20 | 411 |
| | 0.50 | 392 |
| | 0.80 | 280 |
| | 1.00 | 263 |
| Amerhold DR-25 | 0.20 | 186 |
| | 0.50 | 147 |
| | 0.80 | 130 |
| | 1.00 | 178 |
| Ultrahold Strong | 0.20 | 408 |
| | 0.50 | 324 |
| | 0.80 | 572 |
| | 1.00 | 238 |

The data showed that compositions comprising LAN, cationic polymer and various non-neutralized resins are effective systems to retain the curl definition of hair under high humidity.

Effects of the LAN+Non-Neutralized Resin+Cationic Polymer System on Various Hair Types Normal, relaxed and bleached hair are treated with the following system:

| Formula 1 | |
| --- | --- |
| Lecithin | 0.1 |
| Amphoteric Surfactant (30%) | 14.0 |
| Non-ionic Surfactant | 9.3 |
| Luvimer 100 P | 0.5 |
| Polymer JR-30M | 0.5 |
| Sodium Laureth Sulfate (30%) | 30.0 |
| Silicone (e.g., dimethicone) | 2.0 |
| Preservatives | 0.6 |
| Acidifying agent | 0.7 |
| Water | q.s. to 100 |

As a control, treatments were also performed on a similar system that did not contain the non-neutralized resin and the cationic polymer. The results are shown in Table 4.

TABLE 4

Percent Change in Area of Various Hair Types Treated with the LAN + Non-neutralized Resin + Cationic Polymer

| Hair Type | Control | Treated |
|---|---|---|
| Normal | 324 | 216 |
| Relaxed | 327 | 139 |
| Bleached | 295 | 53 |

The data shows that the LAN+non-neutralized resin+cationic polymer system is effective in retaining the curl definition of various hair types at high humidity.

Build-Up Study

Hair was treated with the above Formula 1 that contains 0.5% Amphomer LV-71 and 0.5% Polymer JR-30M one time, five times, and 10 times. The hair that was treated five times was later washed with 15% SLES solution and the percent change in area was determined as described above. The results are shown in Table 5

TABLE 5

Percent Change in Area of Hair Treated with the LAN + Non-neutralized Resin + Cationic Polymer

| Treatment | Percent Change |
|---|---|
| 1X | 135 |
| 5X | 77 |
| 10X | 68 |
| 5X then SLES | 351 |

The data shows that the effectiveness of the LAN+non-neutralized resin+cationic polymer system increased with the frequency of treatment. After multiple treatment washing with SLES, the hair loses its curl definition, indicating that the problems with build-up are not apparent.

Other delivery systems were tried: the following styling cream and styling spray were made:

| Styling Cream | |
|---|---|
| Lecithin | 0.006 |
| Amphoteric surfactants | 0.12 |
| Non-ionic surfactants | 0.02 |
| Film forming polymers | 0.02 |
| Cationic polymer | 0.504 |
| Humectants | 6.000 |
| Thickener | 3.000 |
| Dimethicone | 6.000 |
| Preservatives | 0.408 |
| Acidifying agents | 0.710 |
| Water | q.s. to 100 |

| Styling Spray | |
|---|---|
| Lecithin | 0.006 |
| Amphoteric surfactants | 0.12 |
| Non-ionic surfactants | 0.02 |
| Film forming polymers | 2.52 |
| Cationic polymers | 0.004 |
| Humectant | 3.000 |
| Dimethicone | 2.000 |
| Thickener | 2.5 |
| Alcohol | 5.00 |
| Preservatives | 0.208 |
| pH adjuster | 0.42 |
| Water | q.s. to 100 |

The styling products were applied to people with natural curly hair, after which, the curl definition was retained and no frizziness was observed under high humidity.

In using the invention compositions to, e.g., maintain the shape and/or curl definition of hair, about 0.5-20 g of product can be applied to the hair, as a guide. This can vary based on the length of the hair, the tendency of the hair to frizz, etc., and is within the skill of those of ordinary skill in the art in view of this disclosure.

A preferred embodiment of the invention that one of ordinary skill in the art is now able to make and use in view of this invention description is a composition comprising at least one lecithin, at least one amphoteric surfactant, at least one nonionic surfactant, at least one film forming polymer, and at least one cationic polymer. A highly preferred embodiment of the invention is a composition comprising 0.001-10 wt. % of at least one lecithin, 0.01-30 wt. % of at least one amphoteric surfactant, 0.01-30 wt. % of at least one nonionic surfactant, 0.001-10 wt. % of at least one film forming polymer, and 0.001-15 wt. % of at least one cationic polymer, wherein said wt. %s are based on total weight of said composition, these compositions optionally further comprising water, preferably 1-90 wt % water based on the total weight of the composition. One of ordinary skill is now also able to make and use a method for treating hair comprising applying to hair the compositions according to the invention, particularly preferably to curly hair and/or hair having a tendency to frizz, thus providing a preferred method for maintaining the shape and/or curl definition of hair comprising applying a shape and/or curl definition stabilizing amount of an invention composition to hair in need thereof.

All references, texts, patents, patent applications, product literature, product brochures and MSDS sheets, documents, publications etc., mentioned above are incorporated herein by reference. Where a numeral range or limit is described, all values therewithin are specifically included as if separately written out.

The invention claimed is:

1. A method for inhibiting hair from becoming frizzy when exposed to high humidity, comprising applying a composition to hair in need thereof in an amount sufficient to inhibit hair from becoming frizzy when exposed to high humidity, the composition comprising 0.001-10 wt. % of at least one lecithin, 0.01-30 wt. % of at least one amphoteric surfactant, 0.01-30 wt. % of at least one nonionic surfactant, 0.1 to 15% of at least one film forming polymer, and 0.1 to 15% of at least one cationic polymer, wherein said wt. % s are based on total weight of said composition the at least one film-forming polymer is selected from the group consisting of octylacrylamide/acrylates/butylaminoethyl methacrylate copolymer, PVM/MA half ethyl ester copolymer, Vinyl acetate/crotonates/vinyl neodecanoate copolymer, t-butyl acrylate/ethyl acrylate/methacrylic acid, and acrylic acid/ethyl acrylate/t-butyl acrylamide, the at least one cationic polymer is selected from the group consisting of polyquaternium 4, polyquaternium 6, polyquaternium 7, polyquaternium 10, polyquaternium 11, polyquaternium 16, polyquaternium 22, and polyquaternium 32, and the at least one non-ionic surfactant has an HLB of at least 10.

2. The method according to claim 1, further comprising water and the composition is an aqueous composition.

3. The method according to claim 2, comprising 1-90 wt % water based on the total weight of the composition.

4. The method according to claim 1, wherein the cationic polymer is polyquaternium 10.

5. The method according to claim 1, wherein the composition comprises soy lecithin as the at least one lecithin, disodium cocamphodipropionate as the at least one amphoteric surfactant, and isoceteth-20 as the at least one nonionic surfactant.

6. The method according to claim 1, wherein said composition is a shampoo or a conditioner.

7. The method according to claim 1, wherein said composition is a styling composition.

8. The method according to claim 1, wherein said composition is a deep treatment composition.

9. The method according to claim 1, wherein the at least one nonionic surfactant is formed from a fatty alcohol, a fatty acid, or a glyceride with a C8 to C24 carbon chain.

10. The method according to claim 1, wherein the at least one nonionic surfactant is an ethoxylate, a polyglucoside, or a polysorbate.

11. The method according to claim 1, wherein the at least one nonionic surfactant contain ethoxylate in a molar content of from 10-25.

12. The method according to claim 1, wherein the at least one nonionic surfactant is Laureth-23, Ceteth-10, Ceteth-20, IsoCeteth-20, Steareth-20, Oleth-10, Oleth-20, or alkyl polyglucose.

* * * * *